United States Patent [19]
Bryson

[11] Patent Number: 4,710,182
[45] Date of Patent: Dec. 1, 1987

[54] OSTOMY APPLIANCE AND METHOD OF MAKING

[75] Inventor: Robert M. Bryson, Arlington Heights, Ill.

[73] Assignee: Hollister Incorporated, Libertyville, Ill.

[21] Appl. No.: 937,824

[22] Filed: Dec. 4, 1986

[51] Int. Cl.$^4$ .............................................. A61F 5/44
[52] U.S. Cl. ................................................. 604/339
[58] Field of Search .............................. 604/336–339, 604/332–335

[56] References Cited

U.S. PATENT DOCUMENTS 3,897,781 8/1975 Marsan ................................ 604/338
4,213,458 7/1980 Nolan et al. ........................ 604/344

FOREIGN PATENT DOCUMENTS 1274382 5/1972 United Kingdom ................ 604/337

*Primary Examiner*—C. Fred Rosenbaum
*Assistant Examiner*—J. L. Kruter
*Attorney, Agent, or Firm*—Tilton, Fallon, Lungmus

[57] ABSTRACT

A low-profile ostomy appliance, and a method for producing it, in which a microporous adhesive patch extends about a soft, pliable, barrier ring with the concentric distal (outwardly-facing) surfaces of both the patch and ring being adhesively secured to a connecting ring of soft, flexible, closed-cell, thermoplastic foam, the connecting ring in turn being heat sealed to the wall of a collection pouch about its inlet opening.

18 Claims, 5 Drawing Figures

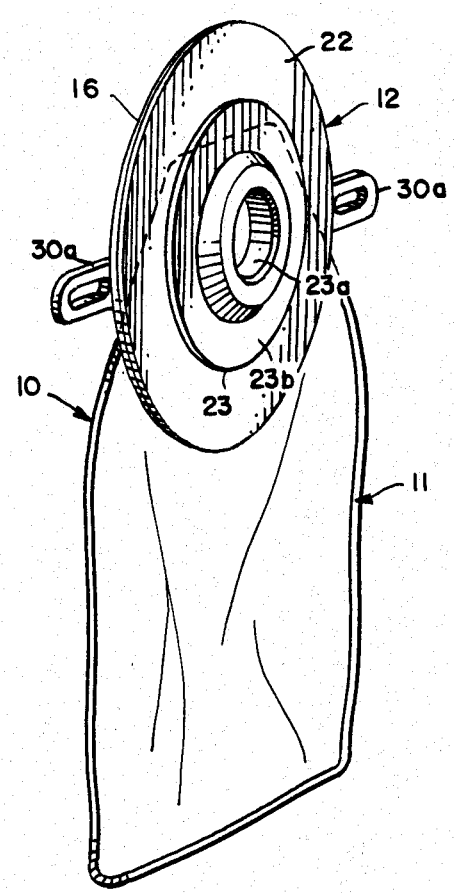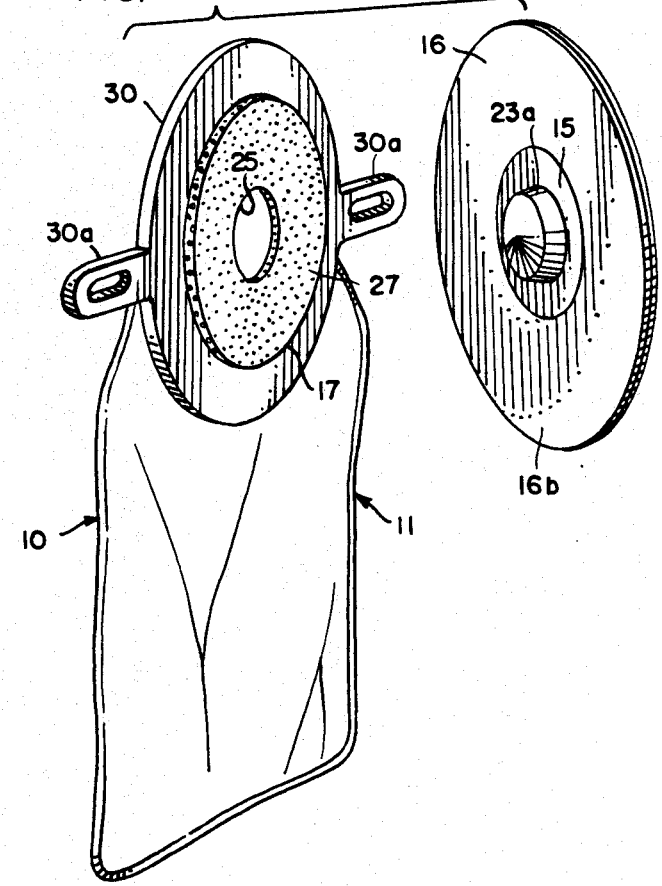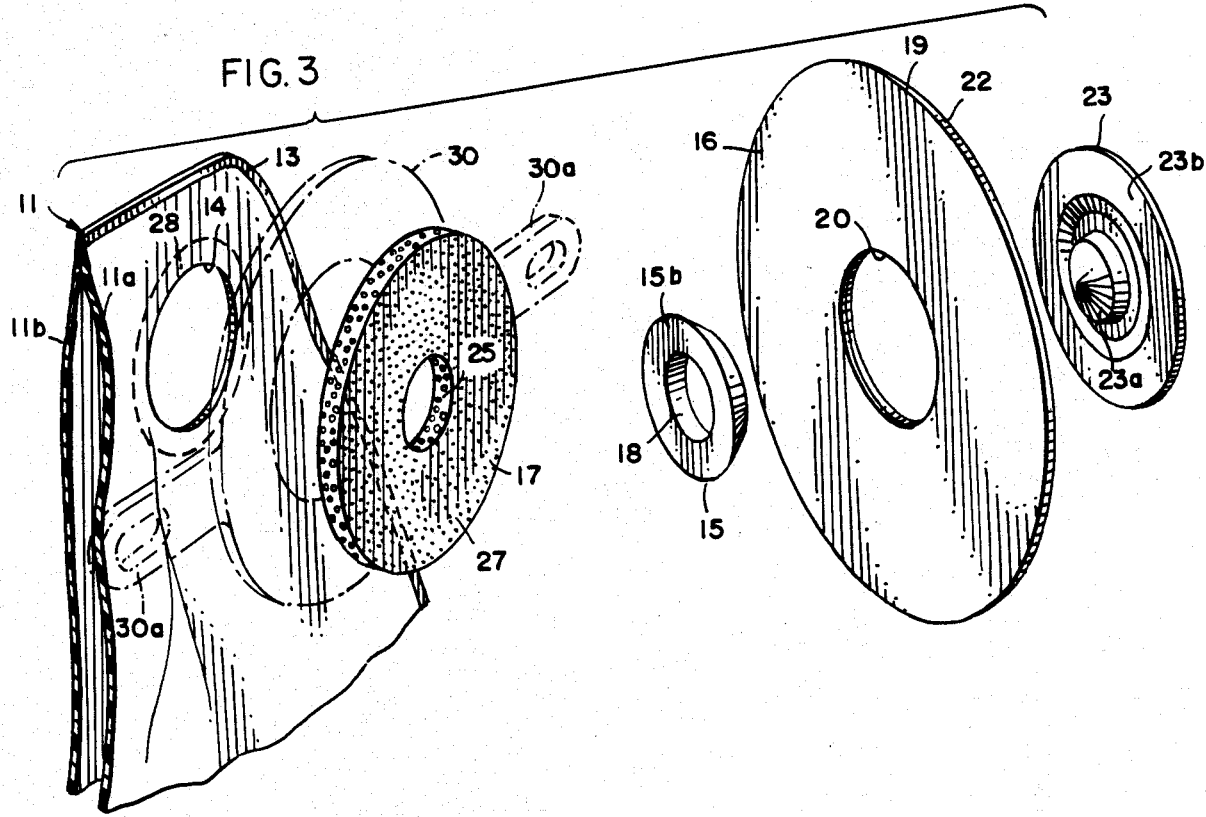

OSTOMY APPLIANCE AND METHOD OF MAKING

BACKGROUND AND SUMMARY

U.S. Pat. No. 4,213,458 discloses an ostomy appliance in which a microporous patch is secured to a thermoplastic ostomy pouch by means of a flexible, non-porous, intermediate attachment ring. The attachment ring functions to distribute forces that might otherwise tear the relatively fragile microporous adhesive patch when the appliance is in use. While it might be thought that tearing problems could be reduced by utilizing microporous fabric of greater thickness, the heat transmission characteristics of microporous material of greater thickness tend to interfere with effective heat sealing of such material to the thermoplastic attaching ring. Less fragile microporous materials might be used, such as those containing reinforcing films or fibers, but then the advantages of greater strength tend to be offset by lower vapor transmission rates. Unless the microporous material has transmission rates for water vapor and other gases that exceed those of a patient's skin, moisture is likely to accummulate between the adhesive patch and the skin resulting in maceration, patient discomfort, and a reduction in the strength of adhesive attachment.

The security of such adhesive attachment, as well as patient comfort and skin condition in the peristomal region, may also be adversely affected by the fluids discharged through the patient's stoma. Protective skin barrier rings formed of karaya or any of a number of other compositions (U.S. Pat. Nos. 4,477,325 and 4,496,357) are therefore commonly used. Such skin barrier materials are soft, pliable, and of high surface tack (both dry and wet), thereby providing semi-solid sealant barriers to protect the skin against the excoriating effects of the stomal effluent. However, such barrier materials characteristically absorb liquid with the result that both liquids and gases may gradually migrate into the microporous patches. Also, effluent coming into contact with the inner edges of a microporous patch may wick outwardly through the patch, thereby causing effluent to reach those areas of the skin contacted by the adhesive patch. A microporous patch may therefore become a pathway for radially outward migration of fluids and gases.

Where a patch or faceplate (whether microporous or not) is secured to a thermoplastic pouch by a heat-sealing operation, a further complication arises, as disclosed in published European patent application 81303312.3 (publication No. 0045587). In the production of an ostomy pouch, the starting material is usually in the form of two webs of thermoplastic material that are advanced stepwise through three manufacturing stations. At the first station, one of the webs is punched to form what will ultimately be the stomal opening in the wall of the pouch. The adhesive patch or faceplate is then heat sealed to the web about that opening, and the two webs are finally brought together and united along their margins by a further heat-sealing operation. Since the margins of the pouch cannot be heat sealed through the faceplate, the result is a construction in which the margins of the faceplate must generally fall within the margins of the pouch. This means that for production reasons the pouch must be made larger than would otherwise be necessary or, conversely, that the faceplate must be smaller than needed or desired. While production techniques are known for overcoming this problem so as to produce an appliance having a faceplate of relatively large size, such procedures tend to be complicated (as indicated in the published application) and therefore expensive.

Other patents illustrative of the state of the art are U.S. Pat. Nos. 3,898,990 and 4,203,445.

A main aspect of this invention therefore lies in providing an ostomy appliance and method which overcome the aforementioned defects and disadvantages of prior constructions and manufacturing procedures. More specifically, the invention involves an improved construction in which the appliance is, or may be, of relatively low profile, has a skin barrier ring of extended life occasioned by the greater thickness of the barrier ring permitted by such construction, and in which the microporous patch is isolated from direct fluid contact even along its edges. The invention allows the use of microporous material of increased thickness (otherwise not feasible because of poor heat transmission characteristics) which, at the same time, has high water vapor transmission properties. The components of the appliance are arranged and constructed so that they are non-wicking in use, present only relatively soft, non-irritating materials for direct contact with the stoma, and permit the use of a rotatable belt-attachment ring for convenient adjustment of the pouch into generally vertical condition for more effective collection of effluent. In addition, the invention results in a construction which permits the use of a faceplate of any desired size regardless of pouch dimensions. In a preferred embodiment, the porous patch of the faceplate has at least a portion of its periphery extending outwardly beyond the peripheral limits of the pouch, yet such a construction is readily manufactured without the complex procedures disclosed in the prior art. Conversely, the present invention permits a reduction of those pouch dimensions that have been required in the past not because they were believed useful for pouch operation but because they were deemed necessary for ease and economy of production.

In brief, the ostomy appliance of this invention comprises an ostomy pouch equipped with a faceplate for adhesive attachment to a patient. The faceplate includes three main components: a skin barrier ring, a microporous patch, and a connecting ring that joins together the skin barrier ring, microporous patch, and pouch. The microporous patch has an enlarged opening that receives and circumscribes the skin barrier ring and, in the preferred embodiment, the distal or outwardly-facing surfaces of both the microporous patch and the skin barrier ring lie along the same plane.

The connecting ring is formed of a thin layer of soft, flexible, liquid and gas impermeable, close-cell, thermoplastic foam. The connecting ring is heat sealed to the pouch about the pouch's stoma opening and, in production, such components are so joined to form a first subassembly. The other subassembly comprises the microporous patch and skin barrier rin supported with their distal surfaces in concentric coplanar relation by means of a disposable supporting cover or cup. The two subassemblies are brought together and adhesively joined with the foam connecting ring being adhesively secured to the distal surfaces of the skin barrier ring and a portion of the microporous patch surrounding the barrier ring. Since the attachment is an adhesive one, the microporous patch may be of any desired outline and size and the upper portion of the pouch may be relatively narrow, thereby avoiding the excessive dimensions commonly found in the upper portions of conventional ostomy pouches.

Other features, advantages, and objects of the invention will become apparent from the specification and drawings.

DRAWINGS

FIG. 1 is a perspective view of an ostomy appliance embodying this invention.

FIG. 2 is a perspective view similar to FIG. 1 but showing the two subassemblies of the appliance just prior to full assembly.

FIG. 3 is an enlarged fragmentary exploded perspective view showing all of the major components of the appliance.

DETAILED DESCRIPTION OF PREFERRED EMBODIMENT

Figure 4:
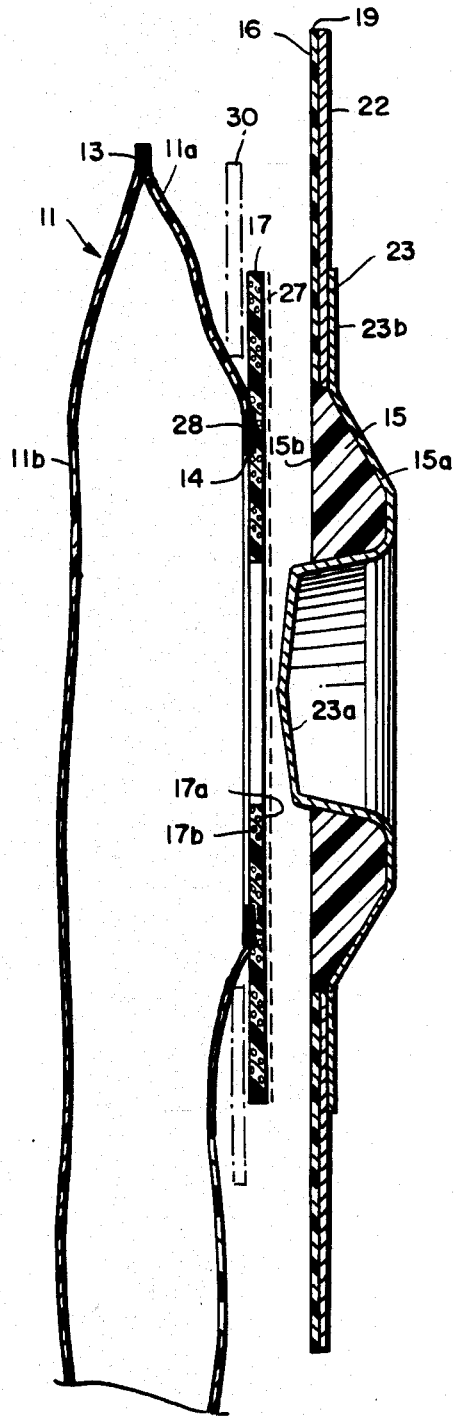
FIG. 4 is an enlarged vertical sectional view of the two subassemblies of the appliance just prior to final assembly, with the optional belt-attachment ring being shown in phantom.

Referring to the drawings, the numeral 10 generally designates an ostomy appliance composed essentially of a collection pouch or bag 11 and a faceplate 12. The pouch is generally flat and includes front and rear walls 11a and 11b sealed together along their peripheral edges by heat seal bond 13. The pouch is conventional except that, as shown in FIGS. 1 and 2, the width of its upper portion (or of its entire vertical extent) may be less than the width of faceplate 12. As is well known, the pouch may be formed of any suitable thermoplastic film such as low-density polyethylene which, if desired, may be coextruded with a barrier core material such as polyvinylidene chloride. Any suitable thermoplastic sheet materials that are impermeable to liquids and gases may be used.

Pouch wall 11a, which may be referred to as a proximal wall or panel because it is in closer proximity to the patient when the appliance is worn, is provided with a stoma-receiving opening 14 near its upper end (FIG. 3). The faceplate 12, which is secured to the proximal wall of the pouch about the stoma opening, essentially comprises a skin barrier ring 15, a microporous adhesive patch 16, and a foam connecting ring 17.

The protective skin barrier ring 15 is formed of a soft, pliable, water-absorbing material having both dry and wet tack. A variety of such compositions are known in the art and may be used for ring 15. Karaya-glycerin formulations, mixtures of polyacrylamide resin and other polyols, and mixtures of elastomers and hydrocolloids may be used. Reference may be had to U.S. Pat. Nos. 4,477,325 and 4,496,357 for a discussion of prior skin barrier compositions and a disclosure of additional compositions having particular advantages which may be utilized here. The skin barrier ring has an opening 18 aligned with but preferably smaller than the stoma opening 14 in the proximal wall of the pouch. The ring diminishes in thickness in a radially outward direction although as shown in the drawings, the distal face 15b of the ring is planar.

The porous patch 16 is advantageously formed of non-woven microporous sheet material of the type disclosed in U.S. Pat. No. 4,213,458. A non-woven microporous material of polyester fibers is believed particularly suitable. The microporous material should have gas and water vapor transmission characteristics sufficiently high to permit the release of water vapor and gases from the skin at a rate high enough to avoid the retention and accummulation of liquid on the surface of the skin covered by the patch. In the embodiment illustrated, the patch has a circular outer edge 19 of a diameter substantially larger than the width of that portion of the pouch 11 to which the faceplate is connected. The patch also includes a central opening 20, a proximal surface 16a, and a distal surface 16b. The diameter of opening 20 is substantially the same as, or slightly greater than, the outside diameter of skin barrier ring 15 and, as depicted most clearly in FIGS. 4 and 5, the distal surface 16b is coplanar with the distal surface 15b of the barrier ring. Proximal surface 16a is coated with an adhesive layer 21 (schematically represented in FIG. 5 by a dotted line) formed of any suitable hypo-allergenic medical-grade pressure-sensitive adhesive that is permeable to gas and water vapor. A typical medical-grade acrylic adhesive has been found effective but other adhesives having similar properties may be used.

The adhesive surface of the patch may be covered by a silicone-coated release sheet 22 and a protective removable cover or cup 23 of developed shape extends over the proximal face 15a of barrier ring 15 and has a central portion 23a that projects into the opening 18 of the barrier ring. The cover also includes an outer skirt portion 23b that overlies the inner portion of release sheet 22 so that to remove the cover a user may easily grasp the skirt portion to peel the cover away from ring 15. The cover with its outwardly-projecting skirt portion also performs the important function of supporting patch 16 and ring 15 in the relationship shown in FIGS. 2 and 4 during the final stages of assembly.

Connecting ring 17 is formed of soft, flexible, liquid and gas impermeable, closed-cell, thermoplastic foam. While any thermoplastic foam having such characteristics may be used, particularly effective results have been obtained using a closed-cell polyethylene foam having a thickness within the range of about 0.5 to 5 millimeters. In its flat undeformed state, the foam connecting ring has planar proximal and distal faces 17a and 17b, respectively. The diameter of central opening 25 is substantially the same as the smallest diameter of opening 18 in barrier ring 15, and the circular outer edge 26 of the connecting ring has a diameter greater than the outside diameter of the barrier ring and the diameter of opening 20 in microporous patch 16. As shown most clearly in FIG. 5, the connecting ring 17 covers the distal surface 16b of the microporous patch to about the same radial extent that it covers the distal surface of barrier ring 15, leaving the outer and far greater surface area of the patch 19 uncovered.

A layer 27 of acrylic adhesive, or other suitable pressure-sensitive adhesive, is interposed between the proximal surface 17a of the connecting ring and the distal surfaces of microporous patch 16 and barrier ring 15 to secure the elements together in the relationship shown in the drawings. The distal side of the thermoplastic connecting ring 17 is secured along an annular heat seal zone 28 to wall 11a of the pouch about stoma opening 14. It will be noted that heat seal zone 28 and opening 14 are both substantially larger than the central openings of the connecting ring and barrier ring.

Appliance 10 also includes a belt-attachment ring 30 shown in solid lines in FIG. 2 and in phantom in FIGS. 3 and 4. The belt-attachment ring may be formed of polyethylene or other tough, durable, and flexible plastic material, and includes a pair of diametrically-disposed outwardly-projecting belt loops 30a with openings for connection to a waist-encircling support belt. Since the construction of the ostomy appliance disclosed herein permits the use of an oversize adhesive faceplate 12, the belt-attachment ring 30 is optional and may not be needed even where a patient is ambulatory and active. If use of a belt-attachment ring is desired, the ring may be easily slipped into place by simply collapsing pouch 11 and inserting it through the opening of ring 30 until the ring is in the position depicted in FIG. 4. It will be observed that the ring 30 is capable of being rotated in relation to pouch 11, thereby allowing a patient to position loops 30a in positions which will assure proper suspension of the pouch when it is finally straped in place.

In the manufacture of the appliance, wall 11a of the pouch is heat sealed to connecting ring 17 before the periphery of proximal wall 11a is sealed to distal wall 11b. The adhesive coating 27 on the proximal face of connecting ring 17 may, if desired, be covered by a suitable release sheet (not shown) during such manufacturing steps. Alternatively, the adhesive coating may be applied to the connecting ring after the ring has been heat-sealed to wall 11a of the pouch. In any event, the pouch with the connecting ring 17 of closed-cell foam heat sealed to the pouch about its stoma opening 14 constitutes a first subassembly.

The second subassembly, as shown in FIGS. 2 and 4, is composed of the protective skin barrier ring 15 and microporous patch 16 (with its release sheet 22 in place) supported by the removable plastic shell or cover 23. In a final manufacturing step, the distal surfaces of the barrier ring and patch are brought into contact with adhesive coating 27 of connecting ring 17. The connecting ring thus becomes the bridging element that securely holds the skin barrier ring 15 and microporous patch 16 in their concentric positions. The cover or shell 23, which previously performed an important role in holding the skin barrier ring and patch together, remains in place until use of the appliance primarily as a protective retaining shield over the tacky surfaces of the barrier ring. When the appliance is to be fitted in place, a user simply peels away the protective shield 23 and the release sheet 22 and adhesively secures the faceplate to the skin surrounding the stoma.

Figure 5:
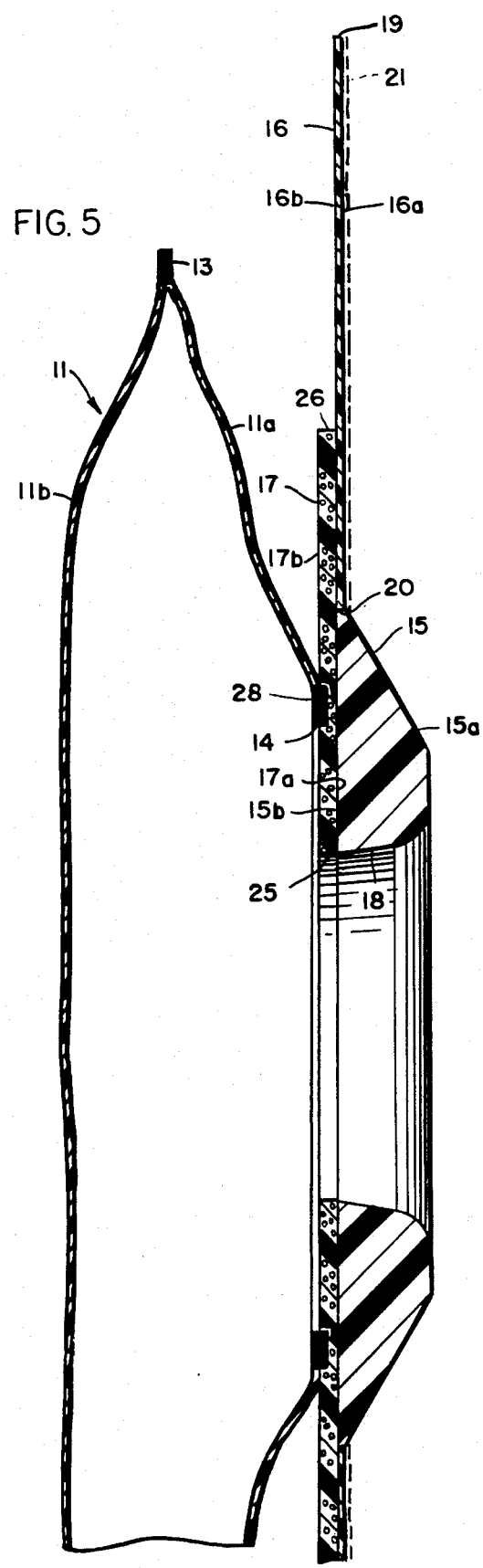
FIG. 5 is a still further enlarged vertical sectional view of a completed appliance in condition for use.

Referring to FIG. 5, it will be observed that the only surfaces of the faceplate capable of making direct contact with the stoma are the surfaces of the barrier ring and foam connecting ring defining openings 18 and 25. Because of its softness and deformability, the foam connecting ring is unlikely to irritate the stoma or cause patient discomfort. The only surface of the skin barrier ring that is exposed to effluent is the annular surface defining opening 18, since the ring's proximal face 15a is in sealing contact with peristomal skin surfaces and the distal face 15b is completely covered and sealed by the liquid-impervious connecting ring 17. Moreover, the adhesive seal between impervious connecting ring 17 and barrier ring 15 prevents liquid and gases from migrating radially outwardly into microporous patch 16. Since the inner edge 20 of the patch is not exposed to effluent, liquid cannot wick outwardly through the patch to produce problems of maceration sometimes encountered in prior constructions.

The microporous patch 19 may be made as large as necessary to provide secure adhesive attachment of the appliance to a patient. This is in contrast to prior constructions where, as brought out in the aforementioned EPC application, earlier production techniques have generally required that the periphery of a faceplate fall within the outer limits of a pouch in order to permit heat sealing of the walls of the pouch together in a subsequent manufacturing step. In the present method, the walls of the pouch are heat sealed together at an earlier stage, during manufacture of the first subassembly, and that subassembly is then joined adhesively, not by heat sealing, to the second subassembly. Since the subassemblies are not connected by heat sealing, there are no constraints on the maximum size of the faceplate or on the minimum size (width, or height above the stoma opening) of the pouch.

Since the foam connecting ring 17 is secured to the microporous patch 16 by adhesive rather than by heat seal, problems of low thermal conductivity that in the past have prevented or discouraged the use of microporous sheet materials of a thickness substantially greater than 4 or 5 mils are no longer presented. In general, the thickness of the microporous patch 16 would be expected to fall within the range of about 4 to 20 mils, with a preferred range being about 8 to 12 mils.

While in the foregoing, I have disclosed an embodiment of the invention in considerable detail for purposes of illustration, it will be understood by those skilled in the art that many of these details may be varied without departing from the spirit and scope of the invention.

I claim:

1. An ostomy appliance comprising an ostomy pouch equipped with a faceplate for adhesive attachment to a patient; said pouch being formed of thermoplastic film and having one wall provided with a stoma opening therein; said faceplate comprising a skin barrier ring, a microporous patch, and a connecting ring joining together said skin barrier ring, microporous patch, and pouch; said skin barrier ring being formed of a soft, pliable, water-absorbing composition having both dry tack and wet tack characteristics; said skin barrier ring also having a proximal face for sealingly engaging the peristomal skin surfaces of a patient and a generally planar distal face; said microporous patch being formed of thin, microporous sheet material having gas and water vapor transmissibility and having planar proximal and distal surfaces; said proximal surface being coated with a pressure-sensitive adhesive and said distal surface being generally coplanar with said distal face of said skin barrier ring; said microporous patch having an opening receiving said skin barrier ring; said connecting ring being formed of soft, flexible, liquid and gas impermeable, closed-cell thermoplastic foam and having an outside diameter substantially greater than said opening of said microporous patch; said connecting ring covering, and being adhesively secured to, the distal face of said skin barrier ring and a concentric portion of the distal surface of said microporous patch about said skin barrier ring; said connecting ring having a distal surface heat sealed to said wall of said pouch in an annular zone about said stoma opening.

2. The appliance of claim 1 in which said connecting ring and said skin barrier ring have aligned openings therethrough; said opening of said skin barrier ring being no smaller than said opening of said connecting ring.

3. The appliance of claim 2 in which said openings of said skin barrier ring and said connecting ring are of substantially equal size.

4. The appliance of claims 2 or 3 in which said openings of said skin barrier ring and said connecting ring are both smaller than said stoma opening of said pouch.

5. The appliance of claim 4 in which said annular heat seal zone securing said pouch and connecting ring together is of substantially greater diameter than said openings of said skin barrier ring and said connecting ring.

6. The appliance of claim 1 in which said distal face of said skin barrier ring and said distal surface of said microporous patch are coplanar.

7. The appliance of claim 1 in which said pouch is flat when empty and includes a second wall having its peripheral portions heat sealed to corresponding peripheral portions of said first mentioned wall; said microporous patch having an outer periphery disposed outwardly beyond said heat sealed peripheral portions of said pouch walls.

8. The appliance of claims 1 or 7 in which said microporous patch is generally circular in outline.

9. The appliance of claim 1 in which said appliance includes a belt-attachment ring; said belt-attachment ring having an opening smaller than the outside diameter of said connecting ring and larger than said annular heat-seal zone joining said connecting ring to said pouch; said belt-attachment ring being rotatable relative to said pouch and being adapted for connection to a supporting belt.

10. The appliance of claim 9 in which said belt-attachment ring is equipped with a pair of generally diametrically-disposed outwardly-projecting belt loops formed integrally therewith.

11. The appliance of claim 1 in which said connecting ring has a thickness within the general range of about 0.5 to 5 millimeters.

12. The appliance of claims 1 or 11 in which said connecting ring is formed of polyethylene foam.

13. The appliance of claim 1 in which said microporous patch is formed of non-woven polyester.

14. The appliance of claim 1 in which said microporous patch has a thickness within the range of about 4 to 20 mils.

15. The appliance of claim 14 in which the thickness of said microporous patch is within the range of about 8 to 12 mils.

16. A method of making an ostomy appliance, comprising the steps of forming a first subassembly by heat sealing a connecting ring of closed-cell thermopolastic foam about the stoma opening of an ostomy pouch formed of thermoplastic film; forming a second subassembly by supporting a skin barrier ring of soft, pliable, tacky, water-absorbing material within the opening of a flat microporous adhesive patch so that adjacent surfaces of said skin barrier ring and said microporous patch are concentric and coplanar; and thereafter adhesively securing both of said concentric coplanar surfaces to that surface of said connecting ring facing away from said pouch so that the opening of said barrier ring is aligned with said stoma opening of said pouch.

17. The method of claim 16 in which said step of adhesively securing said surfaces together includes completely covering said coplanar surface of said barrier ring with said connecting ring.

18. The method of claim 16 in which said connecting ring has an opening of substantially the same size as the opening of said barrier ring, with said rings being adhesively secured together with said openings in axial alignment.

* * * * *